United States Patent [19]

Mihailovski

[11] 4,162,326
[45] Jul. 24, 1979

[54] INSECT CONTROL AGENTS

[75] Inventor: Alexander Mihailovski, Kensington, Calif.

[73] Assignee: Stauffer Chemical Company, Westport, Conn.

[21] Appl. No.: 946,245

[22] Filed: Sep. 27, 1978

[51] Int. Cl.² .................... A61K 31/35; C07D 311/02
[52] U.S. Cl. .............................. 424/283; 260/343.21; 260/345.2; 260/345.5; 568/650; 568/652
[58] Field of Search .................... 260/345.2, 345.5; 424/283

[56] References Cited
PUBLICATIONS
Bhat et al., Tetrahedron, 19, 77 (1963).

Primary Examiner—Nicky Chan
Attorney, Agent, or Firm—Joel G. Ackerman

[57] ABSTRACT

Compounds having the formula

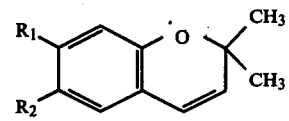

in which one of $R_1$ and $R_2$ is $C_3$–$C_4$ alkynoxy or $C_3$ alkenoxy and the other is hydrogen or methoxy. The compounds have utility as insect control agents, either as insecticides or anti-juvenile hormones.

14 Claims, No Drawings

INSECT CONTROL AGENTS

DESCRIPTION OF THE INVENTION

This invention relates to new insect control agents which are chemicals having the formula

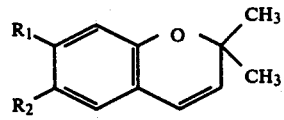

in which one of $R_1$ and $R_2$ is $C_3$–$C_4$ alkynoxy or $C_3$ alkenoxy and the other is hydrogen or methoxy. The compounds have utility as insect control agents and in general as can be seen below act as either insecticides or as anti-juvenile hormones.

The term "insecticide" refers to a compound which has a lethal effect on insects of a type to be controlled, namely that the application of an appropriate amount of such compound results in death of a substantial portion of the insects being treated. The term "anti-juvenile hormone" refers to a compound which affects the development of the insects but does not necessarily have a lethal effect on the insect. Anti-juvenile hormones act so as to counteract the effect of juvenile hormones normally produced by the insect at various times during its life cycle. The juvenile hormones are secreted at various times, causing larvae to molt into the next higher larval or juvenile stage. When it is time for the larvae to molt into a more adult state, such as the pupa, no juvenile hormone is secreted, nor is any juvenile hormone present during the molt from the pupal to adult stage. An anti-juvenile hormone works in the reverse manner, that is, it results in the absence of the juvenile hormone when necessary or the malfunction of such compounds. This causes a larva that should normally molt into a larger larva to instead molt into a pupa, then into a premature or precocious adult. The net effect of the application of the anti-juvenile hormone is that insects grown from their earliest stages in the presence of such compounds will turn into adults much earlier than normal. These adults are usually very small, poorly developed and sterile. An anti-juvenile hormone will work at nearly any time during the larval development stage to create a precocious adult.

For the alkenoxy group in these compounds, the allyloxy group, $CH_2=CHCH_2O-$, is preferred. Among the alkynoxy groups, preferred are 2-propynoxy, $CH\equiv CCH_2O-$ (also known as propargyloxy) and 2-butynoxy, $CH_3C\equiv CCH_2O-$.

In general, the compounds of this invention may be prepared by either of two methods.

METHOD A

A hydroxy-chromanone having formula (I) below, in which $R_2$ is hydrogen or methoxy, and in which the hydroxy group is located at either the 6- or 7- position on the ring and the group $R_2$ at the other of these positions, is alkylated with an alkenyl or alkynyl halide RX (R = $C_3$ alkenyl or $C_3$ or $C_4$ alkynyl) to produce an alkenoxy or alkynoxy chromanone (II) in which one of $R_1$ and $R_2$ is $C_3$–$C_4$ alkynoxy or $C_3$ alkenoxy and the other is hydrogen or methoxy. Compound (II) is then reduced with a suitable reducing agent such as lithium aluminum hydride to produce the corresponding alcohol (III), which is then dehydrated using a mild acid or a mixture of phosphorus oxychloride and pyridine, to the desired product (IV):

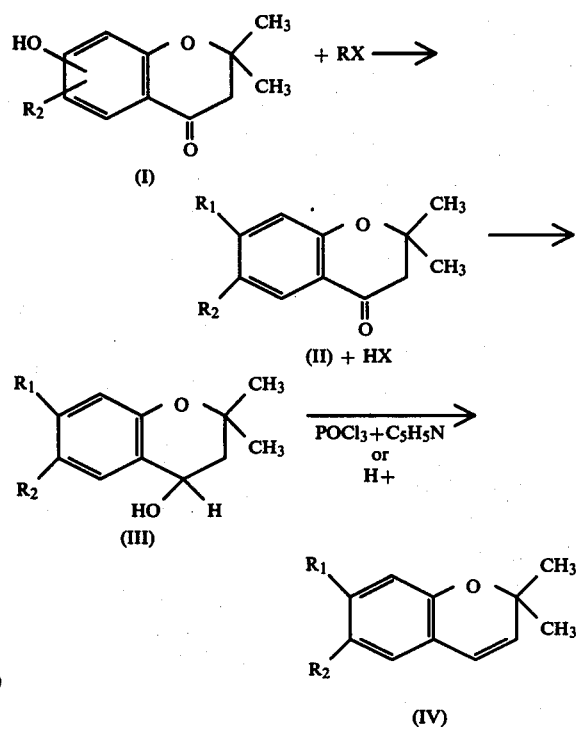

The starting hydroxy chromanone (I) can be prepared by the method described in Bhat, et al., Tetrahedron 19, 77–93 (1963), using appropriate reagents, or by reaction of a resorcinol with, for instance, 3,3-dimethylacrylic acid in the presence of a ring-condensing agent such as polyphosphoric acid.

METHOD B

An appropriately substituted hydroxy-coumarin (V) in which $R_2$ is hydrogen or methoxy and in which the hydroxy group is located at either the 6- or 7- position and the $R_2$ group at the other of these positions, is alkylated with an alkenyl or alkynyl halide RX (R = $C_3$ alkenyl or $C_3$ or $C_4$ alkynyl) to produce an alkenoxy- or alkynoxy-coumarin (VI) in which one of $R_1$ and $R_2$ is $C_3$ alkenoxy or $C_3$–$C_4$ alkynoxy and the other is hydrogen or methoxy. Compound (VI) is treated with at least two molar equivalents of a $C_1$–$C_3$ alkyl-lithium, -sodium or -potassium compound or a $C_1$–$C_3$ Grignard reagent (R'MgX, where X is a halogen) to produce an intermediate compound (VII), which is then cyclized to the desired compound (IV) by heating with glacial acetic acid:

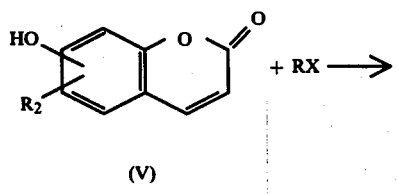

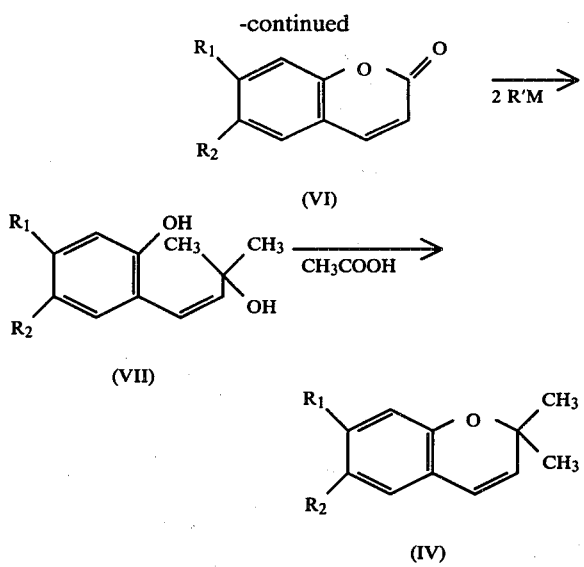

The following are representative examples of preparation of compounds of the present invention.

EXAMPLE 1

Preparation of 2,2-dimethyl-7-(2'-butynoxy)-3-chromanone (Compound 2 herein)

(a) In a reactor were placed 10.0 grams (0.052 mole) 2,2-dimethyl-7-hydroxy-4-chromanone, 13.8 grams (0.10 formula weight) potassium carbonate, 8.9 grams (0.10 mole) 1-chloro-2-butyne, 0.5 grams potassium iodide and 100 milliliters of acetone. The mixture was heated to reflux, then stirred under reflux for 17 hours. There was obtained 10.6 grams of 2,2-dimethyl-7-(2'-butynoxy)-4-chromanone, m.p. 54°–56° C., with confirmation of the structure by nuclear magnetic resonance (NMR) spectroscopy.

(b) Then, 8.3 grams (0.034 mole) of the compound prepared in step (a) was dissolved in 50 milliliters diethyl ether. The solution was slowly added to 50 milliliters of a 1 molar solution of lithium aluminum hydride in diethyl ether. The mixture was stirred at room temperature for 1 hour; then 20 milliliters ethyl acetate was added and the mixture poured into 100 milliliters water. Additional ether was added to dissolve the product; the ether solution was washed with dilute hydrochloric acid and water, dried, filtered and the solvent evaporated to leave a liquid alcohol.

The alcohol was immediately dissolved in 50 milliliters benzene. To the solution was added dropwise a solution of 25 milliliters pyridine and 5 milliliters phosphorus oxychloride in 30 milliliters benzene. The resulting mixture was heated for 1 hour at 90°–100° C., cooled to room temperature and poured into 200 milliliters water. The aqueous layer was extracted twice with benzene (50 milliliters each time). The benzene solutions were combined, washed with 5% hydrochloric acid, then with a saturated sodium bicarbonate solution, then dried over anhydrous magnesium sulfate. The solvent was evaporated to leave 6.1 grams of the desired product, a liquid. The structure of the compound was confirmed by NMR, gas chromatography and mass spectrometry analyses.

EXAMPLE 2

Preparation of 2,2-dimethyl-7-allyloxy-3-chromene (Compound 3 herein)

(a) In a flask were placed 17.3 grams (0.11 mole) 7-hydroxycoumarin, 23.5 grams (0.17 formula weight) potassium carbonate, 13.0 grams (0.17 mole) allyl chloride, 0.5 grams potassium iodide and 200 milliliters acetone. The mixture was refluxed for nineteen hours. There was recovered 18.5 grams of 7-allyloxycoumarin, a colorless solid, m.p. 79°–81° C. The structure of this compound was confirmed by NMR analysis.

(b) In a dry flask was placed 48 milliliters (0.070 mole) of methyllithium dissolved in diethyl ether. To this solution was added a slurry of 5.0 grams (0.025 mole) 7-allyloxycoumarin, prepared as in step (a), in 130 milliliters diethyl ether. A clear solution formed, which was stirred at room temperature for one hour and refluxed for one hour. The mixture was cooled to room temperature; then, 20 milliliters ethanol, 100 milliliters water and 20 milliliters concentrated hydrochloric acid were added (in that order). The organic phase was separated, washed with 100 milliliters water and dried over magnesium sulfate. After evaporation of the solvent, about 6 grams of a liquid hydroxyl group-containing material was obtained.

This intermediate, without being further purified, was stirred for 3 days with 30 milliliters of glacial acetic acid. The majority of the acid was then evaporated, and the residue mixed with 100 milliliters methylene chloride and 100 milliliters water. The organic layer was washed with 10% aqueous sodium hydroxide, dried and the solvent evaporated. The crude product was subjected to a single-stage distillation at a pressure of 4 mmHg and a pot temperature of 130° C. About 1.3 grams of the product was isolated. The structure was confirmed by NMR and mass spectrometry.

The following Table I contains representative examples of compounds of this invention.

TABLE I

| Compound No. | $R_1$ | $R_2$ |
|---|---|---|
| 1 | $CH\equiv CCH_2O-$ | H |
| 2 | $CH_3C\equiv CCH_2O-$ | H |
| 3 | $CH_2=CHCH_2O-$ | H |
| 4 | $CH_3O-$ | $CH\equiv CCH_2O-$ |
| 5 | $CH_3O-$ | $CH_2=CHCH_2O-$ |
| 6 | $CH\equiv CCH_2O-$ | $CH_3O-$ |
| 7 | $CH_2=CHCH_2O-$ | $CH_3O-$ |

Evaluation of Activity

Compounds were tested for anti-juvenile hormone activity and insecticidal activity against the milkweed bug, *Oncopeltus fasciatus* (Dallas) as follows: The test compounds were diluted in acetone and impregnated into a filter paper disc by applying 0.6 milliliters and permitting the solvent to completely evaporate. Ten second-instar nymphs of *Oncopeltus fasciatus* (Dallas) were placed in a petri dish with the treated filter paper. The nymphs were supplied with milkweed seeds and water (by soaking dental cotton in a 4-dram vial cap). All petri dishes were stored at 70° F. The compounds were tested at concentrations ranging from 10 μg/cm² of filter paper downwards. The insecticidal or anti-juvenile hormone effect was determined when control insects had developed into normal adults, normally 3 to 4 weeks.

The results are tabulated in the following Table II. The asterisk in the Table signifies that the indicated compound functioned as an anti-juvenile hormone. Compounds not marked with an asterisk functioned as insecticides, resulting in mortality to at least 50% of the insects at the indicated level.

TABLE II

| Compound No. | ED$_{50}$ or LD$_{50}$, ug/cm² |
|---|---|
| 1 | 2 |
| 2 | 0.5* |
| 3 | 2* |
| 4 | 6 |
| 5 | 8 |
| 6 | 1* |
| 7 | 0.5* |

Thus compounds 2, 3, 6 and 7 function as anti-juvenile hormones while compounds 1, 4 and 5 function as general insecticides.

The compounds of this invention are generally embodied into a form suitable for convenient application. For example, the compounds can be embodies into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite, diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise between about 0.01 and about 90% by weight of the composition.

What is claimed is:

1. A compound having the formula

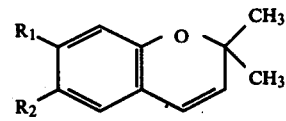

in which one of $R_1$ and $R_2$ is $C_3$–$C_4$ alkynoxy or $C_3$ alkenoxy and the other is hydrogen or methoxy.

2. A compound according to claim 1 in which $R_1$ is $C_3$–$C_4$ alkynoxy or $C_3$ alkenoxy.

3. A compound according to claim 1 in which $R_2$ is $C_3$–$C_4$ alkynoxy or $C_3$ alkenoxy.

4. A compound according to claim 1 in which $R_1$ is 2-propynoxy and $R_2$ is hydrogen.

5. A compound according to claim 1 in which $R_1$ is 2-butynoxy and $R_2$ is hydrogen.

6. A compound according to claim 1 in which $R_1$ is allyloxy and $R_2$ is hydrogen.

7. A compound according to claim 1 in which $R_1$ is methoxy and $R_2$ is 2-propynoxy.

8. A compound according to claim 1 in which $R_1$ is methoxy and $R_2$ is allyloxy.

9. A compound according to claim 1 in which $R_1$ is 2-propynoxy and $R_2$ is methoxy.

10. A compound according to claim 1 in which $R_1$ is allyloxy and $R_2$ is methoxy.

11. A method of controlling insects comprising applying to the insect or habitat thereof an effective controlling amount of a compound having the formula

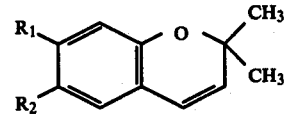

in which one of $R_1$ and $R_2$ is $C_3$–$C_4$ alkynoxy or $C_3$ alkenoxy and the other is hydrogen or methoxy.

12. A method according to claim 11 in which $R_1$ is $C_3$–$C_4$ alkynoxy or $C_3$ alkenoxy.

13. A method according to claim 11 in which $R_2$ is $C_3$–$C_4$ alkynoxy or $C_3$ alkenoxy.

14. An insect controlling composition of matter containing (a) an amount of a compound having the formula

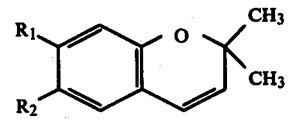

in which one of $R_1$ and $R_2$ is $C_3$–$C_4$ alkynoxy or $C_3$ alkenoxy and the other is hydrogen or methoxy, effective to control an insect and (b) an inert carrier or diluent.

* * * * *

UNITED STATES PATENT AND TRADEMARK OFFICE
CERTIFICATE OF CORRECTION

PATENT NO. : 4,162,326
DATED : July 24, 1979
INVENTOR(S) : Alexander Mihailovski It is certified that error appears in the above-identified patent and that said Letters Patent are hereby corrected as shown below:

In column 5, Table II, under the second heading, please change ---ug/cm$^2$--- to read ---µg/cm$^2$---.

In column 5, line 33, please change the word "embodies" to read "embodied".

Signed and Sealed this

Fourth Day of December 1984

[SEAL]

Attest:

GERALD J. MOSSINGHOFF

Attesting Officer

Commissioner of Patents and Trademarks